United States Patent
Koola

(10) Patent No.: US 7,057,065 B2
(45) Date of Patent: Jun. 6, 2006

(54) PROCESS FOR PRODUCTION OF VINYLPHOSPHONIC ACIDS AND SILYL ESTERS THEREOF

(75) Inventor: Johnson D. Koola, Mount Pleasant, SC (US)

(73) Assignee: Rhodia Inc., Cranbury, NJ (US)

( * ) Notice: Subject to any disclaimer, the term of this patent is extended or adjusted under 35 U.S.C. 154(b) by 83 days.

(21) Appl. No.: 10/393,312

(22) Filed: Mar. 19, 2003

(65) Prior Publication Data

US 2004/0186315 A1    Sep. 23, 2004

(51) Int. Cl.
*C07F 9/28* (2006.01)
(52) U.S. Cl. .......................................................... 562/8
(58) Field of Classification Search ..................... 562/8
See application file for complete search history.

(56) References Cited

U.S. PATENT DOCUMENTS

| | | |
|---|---|---|
| 4,388,252 A | 6/1983 | Dürsch et al. |
| 4,493,803 A | 1/1985 | Kleiner et al. |
| 5,391,815 A | 2/1995 | Roscher |

FOREIGN PATENT DOCUMENTS

| | | |
|---|---|---|
| DE | 2 127 821 | 12/1972 |
| WO | WO 03/016319 | 2/2003 |

OTHER PUBLICATIONS

Robert Rabinowitz, "The Reactions of Phosphonic Acid Esters with Acid Chlorides. A very Mild Hydrolytic Route", Nov. 1963, pp. 2975-2978.
A.J. Gutierrez et al., "Dealkylation of Phosphonate Esters with Chlorotrimethylsilane", 2001, pp. 1299-1302.
Charles E. McKenna et al., "The Facile Dealkylation of Phosphonic Acid Dialkyl Esters By Bromotrimethylsilane", 1977, pp. 155-158.
G. M. Blackburn et al., J.C.S. Chem. Comm., 1978, p. 870.
Y. Machida et al., "A Useful Method for the Dealkylation of Dialkyl Phosphonates", 1979, vol. 9, pp. 97-102.
Hans Gross et al., "Entalkyllerung von Phosphonsäureestern mit labilen funktionellen Gruppen mittels Trimethylsilylbromid", 1978, pp. 344-350.

*Primary Examiner*—Taofiq Solola
*Assistant Examiner*—Ebenezer Sackey

(57) ABSTRACT

A process for preparing vinylphosphonic acid compounds and silyl esters thereof in which a bis(haloalkyl)vinylphosphonate is reacted with an organosilyl halide to produce a silyl ester which can then be converted to the acid by reaction with a proton donor.

21 Claims, No Drawings

PROCESS FOR PRODUCTION OF VINYLPHOSPHONIC ACIDS AND SILYL ESTERS THEREOF

FIELD OF THE INVENTION

The present invention is directed to a process of producing vinylphosphonic acids and silyl esters thereof via the reaction of a vinylphosphonate with an organosilyl halide. The resulting silyl ester of vinylphosphonic acid may be converted to the acid by further reaction with a proton donor.

BACKGROUND OF THE INVENTION

Vinylphosphonic acid is presently manufactured by a variety of processes which are disadvantageous because they are tedious, cumbersome and/or time-consuming. Furthermore, appropriate raw materials for the production of such compounds are not readily commercially available. As a result, multi-step processes have been employed for the manufacture of vinylphosphonic acid. Such processes generally involve prolonged process times, reduced yields and as a result require additional process steps to purify the desired product.

In particular, vinylphosphonic acid may be prepared by the hydrolysis of dialkyl vinylphosphonates such as dimethyl vinylphosphonate. However, such processes are difficult to practice because dialkyl vinylphosphonates such as dimethyl vinylphosphonate are not readily commercially available.

German Patent No. 2,127,821; U.S. Pat. Nos. 4,388,252 and 4,493,803 as well as related patents describe processes for the manufacture of vinylphosphonic acid by a multi-step process including a thermal elimination reaction. The final product requires purification by solvent extraction such as described in U.S. Pat. No. 5,391,815. The multi-step process is both cumbersome and tedious and illustrates the difficulty in introducing vinyl groups to a phosphorous containing compound.

Another process for producing vinylphosphonic acid is described in PCT/GB2002/003573. This process involves the steam hydrolysis of bis(2-chloroethyl)vinylphosphonate under pressure in the presence of formaldehyde. The process takes a significant period of time to go to completion. The reaction produces a very dark colored product which must be treated by an extensive decolorization procedure to obtain a desired product. The reference process illustrates the difficulty in removing chloroethyl groups from bis(2-chloroethyl)vinylphosphonates.

A. J. Gutierrez et al., *Nucleosides, Nucleotides and Nucleic Acids*, Vol. 20 page 1299 (2001) describes the dealkylation of phosphonate esters using organosilyl halides as a potential method for the production of phosphonic acids. R. Rabinowitz, *J. Org. Chem.*, Vol. 28, pg. 2975 (1963) describes the conversion of bis(2-chloroethyl)vinylphosphonate to vinylphosphonic acid by reaction with trimethylsilyl chloride. The reaction requires 30 days for completion making it essentially impractical for any meaningful industrial use. This procedure also demonstrates the difficulty in removing chloroethyl groups from this (2-chloroethyl)vinylphosphonate.

H. Gross et al., *Journal f. prakt. Chemie*, Vol. 320, pg. 344 (1978), C. E. McKenna et al., *Tetrahedron Letters*, Vol. 2, pg. 155 (1977) and G. M. Blackburn et al., *J. C. S. Chem. Comm.*, pg. 870 (1978) describe the preparation of vinylphosphonic acids from vinylphosphonates by reaction with trimethylsilyl bromide or iodide. However, trimethylsilyl bromide and iodide are expensive laboratory reagents and are not readily commercially available raw materials for mass production of vinylphosphonic acids.

It is noted that the H. Gross et al. reference uses vinylphosphonates and trimethylsilyl bromide in a 1:5 molar ratio rendering even the laboratory process, let alone a commercial process extremely expensive.

Y. Machida et al., *Synthetic Communications*, Vol. 9, pg. 97 (1979) describes a reaction between vinylphosphonates, triethylsilyl chloride and lithium iodide in a 1:2.4:2.4 molar ratio in carbon tetrachloride as a solvent. The Machida et al. process employs large amounts of lithium iodide and therefore is disadvantageous because of the possibility of excessive metal contamination of the vinylphosphonic acids with lithium.

It would therefore be a significant advance in the art of producing vinylphosphonic acids if a process could be developed which can be readily implemented on a commercial scale without the disadvantages described above characteristic of prior art processes. It would be a further advance in the art to produce silyl ester intermediate products of the desired vinylphosphonic acids.

SUMMARY OF THE INVENTION

The present invention is generally directed to a process of producing vinylphosphonic acids in which a bis(2-haloalkyl)vinylphosphonate is reacted with an organic silyl halide to produce the silyl ester of vinylphosphonic acid which can then be converted to the acid by treatment with a proton donor.

In a particular aspect of the present invention, there is provided a process of producing a compound of Formula IA:

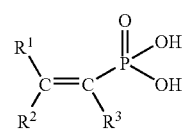

wherein each of $R^1$–$R^3$ is independently selected from the group consisting of hydrogen, halogen and a substituted or unsubstituted alkyl group and aryl group, said process comprising reacting a compound of Formula II:

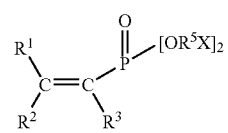

wherein $R^5$ is a substituted or unsubstituted alkyl group and X is a halogen with an organosilyl halide of Formula III:

wherein $R^4$ is selected from the group consisting of a substituted or unsubstituted alkyl group, aryl group and alkoxy group, X is halogen and n is an integer of from 1 to 3. The resulting silyl ester intermediate compound is then reacted with a proton donor to produce a compound of Formula IA.

The silyl ester intermediate compound may be isolated from the reaction mixture and later processed to form the compound of Formula IA.

DETAILED DESCRIPTION OF THE INVENTION

The present invention is directed to a production of vinylphosphonic acids of Formula IA and the intermediate products in the form of silyl esters which vary in structure according to the particular organosilyl halide used in the reaction. The process commences by reacting a compound of Formula II

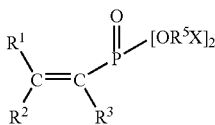

wherein $R^1$, $R^2$ and $R^3$ are independently selected from the group consisting of hydrogen, halogen, and a substituted or unsubstituted alkyl group and aryl group, $R^5$ is a substituted or unsubstituted alkyl group and X is a halogen. The compound of Formula II is reacted with an organosilyl halide of Formula III

 (III)

wherein $R^4$ is selected from the group consisting of a substituted or unsubstituted alkyl group, aryl group and alkoxy group, X is a halogen and n is an integer from 1 to 3. This one step reaction produces a silyl ester, the structure of which depends on the value of n. When n is 1, the reaction of the organosilyl halide of Formula III with the compound of Formula II will result in the formation of a silyl ester intermediate product of Formula IB

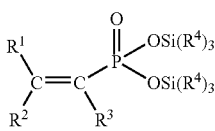

wherein $R^1$–$R^4$ are as defined above. The compound of Formula IB may then be converted to vinylphosphonic acid by reaction with a proton donor such as water or an alkanol, typically a lower alkanol such as methanol, ethanol and the like.

When the compound of Formula III has an n value of 2, its reaction with the compound of Formula II will result in the formation of an oligomeric silyl ester having a repeating structure encompassed by Formula IC

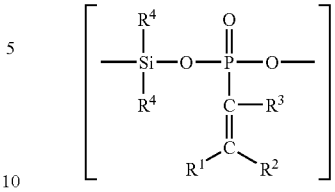

wherein $R^1$–$R^4$ is as described above. The compound of Formula IC may then be reacted with a proton donor as described above to produce the vinylphosphonic acid of Formula IA.

If an organosilyl halide of Formula IC is chosen with an n value of 3, its reaction with the compound of Formula II will result in the formation of a silyl ester intermediate product having repeating units shown in Formula ID

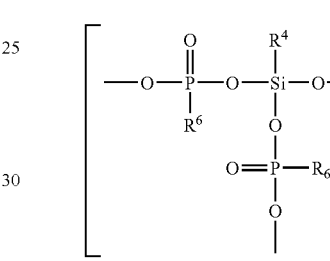

wherein $R^4$ is as defined above and $R^6$ is represented by groups covered by Formula IV

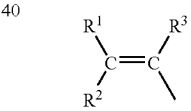

wherein $R^1$–$R^3$ are as defined previously. The silyl ester intermediate product of Formula ID may then be reacted with a proton donor as described above to form the desired vinylphosphonic acid.

As used herein the term "alkyl group" shall mean an alkyl group having from 1 to 12 carbon atoms. Lower alkyl groups are a preferred class of alkyls and have from 1 to 6 carbon atoms. The term "aryl group" includes non-heterocyclic ring structures such as phenyl, benzyl, naphthyl and the like.

The preferred group for $R^5X$ is a lower haloalkyl group, most preferably 2-haloethyl. The preferred halogen is chlorine. The preferred substituent for $R^1$–$R^3$ is hydrogen.

The substituents which may be attached to the alkyl groups, the aryl groups and the alkoxy groups may be selected from alkyl groups and aryl groups.

The preferred compound of Formula II is bis(2-chloroethyl)vinylphosphonate in which each of $R^1$–$R^3$ is hydrogen and $R^5X$ is 2-chloroethyl.

The compound of Formula II is reacted with an organosilyl halide of Formula III in which $R^4$ is selected from the group consisting of substituted or unsubstituted alkyl groups, aryl groups and alkoxy groups. A preferred class of organosilyl halides includes triethylsilyl chloride, triethylsilyl bromide, trimethylsilyl chloride, trimethylsilyl bromide, dimethylsilyl dichloride, dimethylsilyl dibromide, diethylsilyl dichloride, diethylsilyl dibromide, methylsilyl trichloride and methylsilyl tribromide. A preferred compound of Formula III when n is 1 is trimethylsilyl chloride. A preferred compound of Formula III when n is 2 is dimethylsilyl dichloride. A preferred compound of Formula III when n is 3 is methylsilyl trichloride.

The process of the present invention is generally conducted at a temperature of from about 50 to 250° C. and from a pressure of from about 1 to 10 atmospheres. The preferred reaction conditions include a temperature of from about 120 to 160° C. and a pressure of from 3 to 5 atmospheres.

The amount of the organosilyl halide reacted with the compound of Formula II will typically be at least a stochiometric amount. When the n value is 1, the preferred amount of the organosilyl halide is at least 2 equivalents, more preferably from about 2 to 3 equivalents.

The reaction of the compound of Formula II with the organosilyl halide of Formula III can be accelerated by the addition of a reaction accelerator which can include halogens such as bromine and iodine and metal halides such as lithium iodide and the like. The amount of the reaction accelerator will be an amount which is sufficient to accelerate the reaction beyond what can be expected by the reaction of the compound of Formula II with the organosilyl halide of Formula III. A suitable amount of the reaction accelerator is well within the skill of the art and will generally be in the range of from about 0.1 to 0.5 mol%.

The reaction of the compound of Formula II with the organosilyl halide of Formula III will result in the production of silyl esters (i.e. organosilyl vinylphosphonates) of Formulas IB–ID. Typical byproducts will include 1,2-dihaloalkanes and any residual organosilyl halides, which may be easily removed from the intermediate product of Formulas IB–ID by distillation.

The intermediate compounds of Formulas IB–ID are then treated with a proton donor such as water or alkanol (e.g. ethanol) to produce vinylphosphonic acid. Any residual byproduct such as disiloxane can readily be removed through convenient phase separation processes.

The vinylphosphonic acid produced in accordance with the present invention is an almost colorless aqueous solution which does not require separate steps of purification and/or decolorization. An aqueous solution of vinylphosphonic acid may be concentrated to any desired degree by removal of water by, for example, vacuum distillation.

The present process provides a convenient and low cost way of producing vinylphosphonic acids and intermediate silyl esters thereof through readily available starting materials under reaction conditions which can readily be employed on a commercial scale.

EXAMPLE 1

151 g (0.648 mole) of bis(2-chloroethyl)vinylphosphonate and 226 g (2.080 moles) of trimethylsilyl chloride were charged into a 500 mL glass pressure reactor under a nitrogen atmosphere. The reactor was equipped with magnetic stirring, pressure gauge, stoppers and needle valves (inlet/outlet) and a heat source. The reactor was closed, cooled in an ice bath and evacuated to ~18" of Hg. The reactor under vacuum was set for heating. The reaction temperature was slowly raised to ~145 to 150° C. while rapidly increasing the pressure to about 4 atmospheres. Care was taken not to exceed the pressure limits of the reactor. After nearly 24 hours of reaction time, the reactor was cooled down, the pressure reduced and the reactor materials were transferred into a distillation set up. Volatiles like dichloroethane and any residual trimethylsilyl chloride were removed by distillation under vacuum to produce the intermediate product the bis(silyl)ester.

The intermediate product was stirred with 81 g of water for about 1 hour. Two layers were observed which were phase separated. The bottom aqueous layer was confirmed to be vinylphosphonic acid by NMR analysis. The top organic layer was identified as hexamethyldisiloxane, which contained no detectable quantities of phosphorus containing materials. Vinylphosphonic acid was obtained in a yield exceeding 95%.

EXAMPLE 2

2.33 g (10 mmol) of bis(2-chloroethyl)vinylphosphonate and 4.60 g (30.5 mmol) of triethylsilyl chloride were charged under a nitrogen blanket into a 100 mL round bottom flask fitted with a condenser. The reaction mixture was kept stirred magnetically and slowly heated to 170° C. for about 24 hours. After cooling down the reactor, the crude product was stirred with 10 g of water for about 2 hours. Two layers were observed. The bottom aqueous layer was confirmed to be vinylphophonic acid by NMR analysis.

What is claimed is:
1. A process of producing a compound of Formula IA:

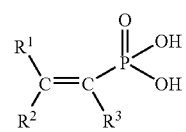

IA wherein each of $R^1$–$R^3$ is independently selected from the group consisting of hydrogen, halogen and a substituted or unsubstituted alkyl group and aryl group, said process comprising reacting a compound of Formula II:

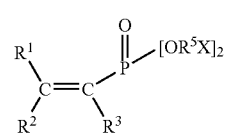

II wherein $R^5$ is a substituted or unsubstituted alkyl group and X is a halogen with an organosilyl halide of Formula III:

(III)

wherein $R^4$ is selected from the group consisting of a substituted or unsubstituted alkyl group, aryl group, and alkoxy group and X is as defined above and n is an integer of from 1 to 3, to form an intermediate compound and reacting the intermediate compound with a proton donor to produce the compound of Formula IA.

2. The process of claim 1 wherein the compound of Formula III has an n value of 1 and the intermediate compound is a compound of Formula IB

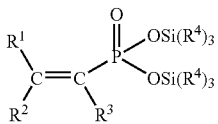

IB wherein $R^1$–$R^4$ are as defined above.

3. The process of claim 2 wherein the compound of Formula III is selected from the group consisting of trimethylsilyl chloride, trimethylsilyl bromide, triethylsilyl chloride and triethylsilyl bromide.

4. The process of claim 3 wherein the compound of Formula III is trimethylsilyl chloride.

5. The process of claim 1 wherein the compound of Formula III has an n value of 2 and the intermediate compound has repeating units represented by Formula IC

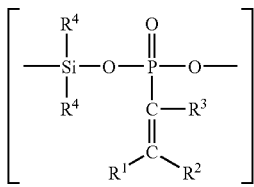

IC wherein $R^1$–$R^4$ is as described above.

6. The process of claim 5 wherein the compound of Formula III is selected form the group consisting of dimethylsilyl dichloride, dimethylsilyl dibromide, diethylsilyl dichioride and diethylsilyl dibromide.

7. The process of claim 6 wherein the compound of Formula III is diethylsilyl dichioride.

8. The process of claim 1 wherein the compound of Formula III has an n value of 3 and the intermediate compound has repeating units represented by Formula ID

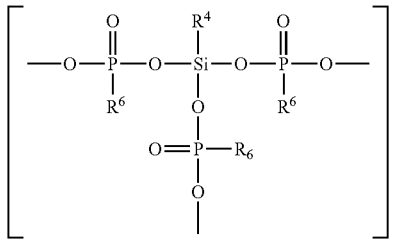

ID wherein $R^4$ is as defined above and $R^6$ is represented by groups covered by Formula IV

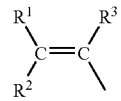

IV wherein $R^1$–$R^4$ are as defined previously.

9. The process of claim 8 wherein the compound of Formula III is selected from the group consisting of methylsilyl trichloride, methylsilyl tribromide, ethylsilyl trichloride and ethylsilyl tribromide.

10. The process of claim 9 wherein the compound of Formula III is methylsilyl trichloride.

11. The process of claim 1 comprising conducting the process at a temperature of from about 50 to 250° C. at from about 1 to 10 atmospheres.

12. The process of claim 11 comprising conducting the process at a temperature of from about 120° C. to 160° C. at a pressure of from about 3 to 5 atmospheres.

13. The process of claim 1 comprising reacting the compound of Formula II with at least a stoichiometric amount of the compound of Formula III.

14. The process of claim 13 comprising reacting the compound to Formula II with at least two equivalents of the compound of Formula III when n is 1.

15. The process of claim 14 comprising reacting the compound of Formula II with 2 to 3 equivalents of the compound of Formula III when n is 1.

16. The process of claim 1 further comprising conducting the process in the presence of an effective amount of a reaction accelerator.

17. The process of claim 16 wherein the reaction accelerator is a halogen containing compound.

18. The process of claim 17 wherein the halogen containing compound is selected from the group consisting bromine, iodine, and lithium iodide.

19. The process of claim 16 wherein the effective amount of the reaction accelerator is from about 0.1 to 0.5 mol%.

20. The process of claim 1 further comprising after the reaction of compounds of Formula II and III, removing any unreacted compound of Formula III and any dihaloalkanes which may have formed.

21. The process of claim 1 wherein the proton donor is selected from the group consisting of water and alkanols.

* * * * *